US010646319B2

(12) United States Patent
Johansson et al.

(10) Patent No.: US 10,646,319 B2
(45) Date of Patent: May 12, 2020

(54) THIN, FLEXIBLE POWERED ORAL CARE DEVICE

(71) Applicant: COLGATE-PALMOLIVE COMPANY, New York, NY (US)

(72) Inventors: Patrik Johansson, Hoboken, NJ (US); John Jacob Gatzemeyer, Hillsborough, NJ (US); Harsh Mahendra Trivedi, Hillsborough, NJ (US); James Gerard Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 17 days.

(21) Appl. No.: 14/983,734

(22) Filed: Dec. 30, 2015

(65) Prior Publication Data

US 2017/0189153 A1 Jul. 6, 2017

(51) Int. Cl.
| | |
|---|---|
| *A61C 19/06* | (2006.01) |
| *A61K 8/23* | (2006.01) |
| *A61K 8/24* | (2006.01) |
| *A61K 8/33* | (2006.01) |
| *A61Q 11/02* | (2006.01) |
| *A61Q 11/00* | (2006.01) |
| *A61N 1/05* | (2006.01) |
| *C25B 1/00* | (2006.01) |
| *C25B 9/06* | (2006.01) |

(52) U.S. Cl.
CPC .......... *A61C 19/066* (2013.01); *A61C 19/06* (2013.01); *A61C 19/063* (2013.01); *A61K 8/23* (2013.01); *A61K 8/24* (2013.01); *A61K 8/33* (2013.01); *A61N 1/0548* (2013.01); *A61Q 11/00* (2013.01); *A61Q 11/02* (2013.01); *C25B 1/00* (2013.01); *C25B 9/06* (2013.01)

(58) Field of Classification Search
CPC ............................. A61C 19/066; A61K 6/005
USPC ....................................................... 433/29, 32
See application file for complete search history.

(56) References Cited

U.S. PATENT DOCUMENTS

| | | | | |
|---|---|---|---|---|
| 4,398,545 | A * | 8/1983 | Wilson | A61N 1/0456 |
| | | | | 607/152 |
| 6,886,208 | B2 * | 5/2005 | Kemp | A61C 17/22 |
| | | | | 15/105 |
| 7,645,137 | B2 | 1/2010 | Wasyluch | |
| 7,743,447 | B2 | 6/2010 | Kemp et al. | |
| 8,468,870 | B2 | 6/2013 | Hennig et al. | |
| 2005/0004509 | A1 * | 1/2005 | Sun | A61N 1/30 |
| | | | | 604/20 |

(Continued)

FOREIGN PATENT DOCUMENTS

| | | |
|---|---|---|
| EP | 1525857 | 2/2007 |
| KR | 1020140148176 | 12/2014 |

(Continued)

OTHER PUBLICATIONS

International Search Report and the Written Opinion issued in International Application PCT/US2016/068286 dated Mar. 17, 2017.

*Primary Examiner* — Yogesh P Patel
*Assistant Examiner* — Stephen R Sparks

(57) ABSTRACT

In some embodiments, an oral care device includes a flexible base substrate, a power source disposed on the base substrate, and first and second electrodes electrically connected to the power source. Also disclosed are methods of using the same, for example, for whitening the teeth or for treating other conditions in the oral cavity.

29 Claims, 4 Drawing Sheets

(56) References Cited

U.S. PATENT DOCUMENTS

| | | |
|---|---|---|
| 2005/0010161 A1 | 1/2005 | Sun et al. |
| 2006/0234189 A1* | 10/2006 | Duret .................. A61C 19/06 433/215 |
| 2008/0032253 A1 | 2/2008 | Montgomery et al. |
| 2008/0199830 A1* | 8/2008 | Fontenot ............... A61C 19/06 433/215 |
| 2009/0092643 A1 | 4/2009 | De Vreese et al. |
| 2010/0151407 A1 | 6/2010 | Rizoiu et al. |
| 2010/0200158 A1 | 8/2010 | Lindquist et al. |
| 2015/0004556 A1 | 1/2015 | Jin et al. |
| 2015/0191845 A1* | 7/2015 | Scherson ............... C25D 17/10 417/48 |

FOREIGN PATENT DOCUMENTS

| | | |
|---|---|---|
| WO | WO 2006/108432 | 10/2006 |
| WO | 2014/066576 | 5/2014 |

\* cited by examiner

THIN, FLEXIBLE POWERED ORAL CARE DEVICE

BACKGROUND

Various products and processes have been developed to maintain oral health. While several conventional products and processes may be administered at home, still others require professional assistance or oversight. For example, some conventional teeth whitening procedures require bulky and/or expensive light sources to emit controlled light on the teeth. Often, take-home products are less effective than products or processes administered by professionals, but the inconvenience, cost, and/or unknown of visiting a professional may prohibit seeking professional help.

Accordingly, there is a need in the art for compact, effective oral care devices. This disclosure is directed at overcoming one or more problems set forth above and/or other problems of the prior art.

BRIEF SUMMARY

This application describes improved oral care implements and methods for treating the oral cavity. In some embodiments, an oral care device herein may be embodied as a flexible strip for placement in the oral cavity. The flexible strip may include a base substrate, a power source disposed on the base substrate, and one or more components disposed on the base substrate in electrical communication with the power source. Other layers or substrate may also be provided. For example, an adhesive may be provided to promote retention of the device in the oral cavity. Moreover, a release layer may be provided, for example, to protect the components of the oral care device until it is ready for use. Removal of the release layer may expose components of the device, such as the adhesive, and/or may trigger some action of the device, such as by switching on the power source or otherwise enabling electrical communication within the device.

In some implementations, electrodes are provided as the component in electrical communication with the power source. The power source provides a current to the electrodes. In some instances, the electrodes may be used to provide an electrochemical benefit. For example, the electrode may be used to provide an electrical potential to an activating agent. In some implementations, the activating agent may be an orally acceptable sulfate and/or bisulfate in a buffered, electrically conductive medium that, with the introduction of current via the electrode, facilitates in situ production of persulfate ($S_2O_8^{2-}$). Alternatively, the activating agent may be a sacrificial metal, e.g., zinc, that oxidizes in the presence of the electrical potential to release $Zn^{2+}$. Zinc ions are conventionally known to provide oral health benefits including e.g., anti-bacterial benefits. In still other embodiments, one or more of the electrodes, e.g., an anode of the electrode, may include a sacrificial metal that degrades to provide an oral benefit. For example, the anode of the electrode may include zinc and application of current to the electrode may cause the zinc in the anode to oxidize, releasing beneficial zinc ions into the oral cavity.

In some implementations, a flexible light source, such as a polymer LED, may be provided as the component in electrical communication with the power source. More specifically, the light source is powered by the power source. Control circuitry may also be provided on the base substrate, to control the light source. For instance, it may be desirable to control the wavelength of light emitted from the light source, a duration of irradiation by light from the light source, or other characteristics of the emitted light. When the oral care device includes a light source, a reflective surface may also be provided, e.g., to direct the irradiating light in a preferred direction.

In other implementations, methods for whitening teeth, for oxidizing volatile sulfur compounds that give rise to halitosis, for killing bacteria on the teeth in the mouth, and/or for providing other oral benefits are provided. For instance, methods according to this disclosure may include activating the power source on a device such as described above and placing the device in the oral cavity. Adhesive or the like may be provided to assist in retaining the device. Depending upon the application, the device may be positioned proximate a location to be treated, such as proximate a tooth or teeth to be whitened, while in other applications specific placement of the device is not required.

In aspects of this disclosure, An oral care device includes a base substrate; a power source disposed on a surface of the base substrate; and an electrode layer disposed on the surface of the base substrate or the power source. The electrode layer includes a first electrode comprising a first flexible metallic strip electrically connected to the power source and a second electrode comprising a second flexible metallic strip electrically connected to the power source and substantially parallel to the first metallic strip. The electrode layer is disposed such that a length of the first electrode and a length of the second electrode are substantially parallel to a longitudinal axis of the base substrate.

In one or more additional aspects, in an oral care device as described in the preceding paragraph, at least one of the first electrode and the second electrode includes a sacrificial metal that degrades upon application of current to the plurality of electrodes to release ions to the oral cavity.

In one or more additional aspects, in an oral care device as described in any of the preceding paragraphs, the sacrificial metal may include zinc, and the zinc may oxidize upon application of current to the plurality of electrodes to release zinc ions.

In one or more additional aspects, in an oral care device as described in any of the preceding paragraphs, an active substance may be included.

In one or more additional aspects, in an oral care device as described in the preceding paragraph, the active substance may include at least one of a tooth whitener or an antibacterial.

In one or more additional aspects, in an oral care device as described in any of the preceding paragraphs, the active substance may include a persulfate, a monoperoxy sulfate, a chloride, a phosphate, or a carbonate.

In one or more additional aspects, in an oral care device as described in any of the preceding paragraphs, the active substance is formed as a paste or gel and disposed on a side of the plurality of electrodes opposite the flexible base substrate.

In one or more additional aspects, in an oral care device as described in any of the preceding paragraphs, the active substance may be disposed on an active layer substrate, and the active layer substrate may be disposed on a side of the plurality of electrodes opposite the flexible base substrate.

In one or more additional aspects, in an oral care device as described in any of the preceding paragraphs, an adhesive layer may be disposed to retain the oral care device in a position in the oral cavity.

In one or more additional aspects, in an oral care device as described in any of the preceding paragraphs, a removable release layer may be provided.

In one or more additional aspects, in an oral care device as described in the preceding paragraph, the release layer may be disposed over an adhesive, and removal of the release layer may expose the adhesive.

In one or more additional aspects, in an oral care device as described in any of the preceding paragraphs, the release layer may be disposed such that removal of the release layer activates the power source or completes a circuit between the power source and the plurality of electrodes.

In one or more additional aspects, in an oral care device as described in any of the preceding paragraphs, the power source may be a polymer battery.

In one or more additional aspects, in an oral care device as described in any of the preceding paragraphs, control circuitry may be provided in electrical communication with the power source to control current between the power source and the first and second electrodes.

In another aspect of this disclosure, a method of treating a condition in an oral cavity may include providing a flexible oral care device comprising a flexible base substrate, a flexible power source disposed on a side of the base substrate, and first and second elongate electrodes disposed on the flexible base substrate or the power source and electrically connected to the power source; retaining the flexible oral care device on a surface in the oral cavity; and powering on the power source to generate an electrical field between the first and second electrodes.

In one or more additional aspects, a method as described in the preceding paragraph may further include providing an active substance in the oral cavity, proximate to at least one of the first and second electrodes.

In one or more additional aspects, in a method as described in one of the two preceding paragraphs, the active substance may include an active layer disposed on the flexible oral care device.

In one or more additional aspects, a method as described in any of the three preceding paragraphs may include folding the flexible oral care device along a longitudinal axis between a first longitudinal side of the flexible oral care device and a second longitudinal side of the flexible oral care device. Retaining the flexible oral care device on the surface of the oral cavity may include retaining a portion of the first longitudinal side of the flexible oral care device on a first side of at least one tooth in the oral cavity and retaining a portion of the second longitudinal side of the flexible oral care device on a second side the at least one tooth.

In one or more additional aspects, in a method as described in any of the four preceding paragraphs, the flexible oral care device may further include a release layer and powering on the power source comprises removing the release layer.

In one or more additional aspects, in a method as described in one of the five preceding paragraphs, one of the first and second electrodes may include zinc.

In one or more additional aspects, in a method as described in any of the six preceding paragraphs, an active agent may include an inert salt that generates a whitening agent in the electrical field.

In one or more additional aspects, in a method as described in the preceding paragraph, the inert salt may include a sulfate that generates persulfate in the electrical field.

In an additional aspect of this disclosure, an oral care device includes a flexible base substrate; a power source disposed on a side of the flexible base; and a flexible light source disposed on the flexible base or on the power source and in electrical communication with the power source.

In one or more additional aspects, an oral care device as described in the preceding paragraph may also include a reflective surface disposed to reflect light emitted from the light source in a predetermined direction.

In one or more additional aspects, in an oral care device as described in one of the two preceding paragraphs, the power source may include a flexible organic light emitting diode or a polymer light emitting diode.

In one or more additional aspects, in an oral care device as described in the preceding paragraph, the reflective surface may include a reflective film disposed on a surface of the base substrate.

In one or more additional aspects, an oral care device as described in one of the four preceding paragraphs may further include an active substance.

In one or more additional aspects, in an oral care device as described in the preceding paragraph, the active substance may include at least one of a tooth whitener, a light-activated intercalator, or a photosensitizer.

In one or more additional aspects, in an oral care device as described in one of the two preceding paragraphs, the active substance may be formed as a paste or gel and disposed on a side of the plurality of the flexible light source opposite the flexible base substrate.

In one or more additional aspects, in an oral care device as described in one of the three preceding paragraphs, the active substance may be disposed on an active layer substrate, and the active layer substrate may be disposed on a side of the plurality of electrodes opposite the flexible base substrate.

In one or more additional aspects, an oral care device as described in one of the eight preceding paragraphs may further include an adhesive layer disposed to retain the oral care device in a position in the oral cavity.

In one or more additional aspects, an oral care device as described in one of the nine preceding paragraphs may further include comprising a removable release layer.

In one or more additional aspects, in an oral care device as described in the preceding paragraph, the release layer may be disposed over an adhesive, and removal of the release layer may expose the adhesive.

In one or more additional aspects, in an oral care device as described in one of the two preceding paragraphs, the release layer may be disposed such that removal of the release layer activates the power source or completes a circuit between the power source and the light source.

In one or more additional aspects, in an oral care device as described in one of the twelve preceding paragraphs, the power source may be a polymer battery.

In one or more additional aspects, an oral care device as described in any of the thirteen preceding paragraphs may further include control circuitry in electrical communication with the light source to control light emitted from the power source and the first and second electrodes.

In an additional aspect, a method of treating a condition in an oral cavity may include providing a flexible oral care device comprising a flexible base substrate, a flexible power source disposed on a first side of the base substrate, and a flexible light source on the flexible base substrate or the power source and electrically connected to the power source; retaining the flexible oral care device on a surface in the oral cavity; and powering on the power source to irradiate the surface in the oral cavity.

In one or more additional aspects, a method according to the preceding paragraph may further include controlling at least one of a wavelength, an intensity, or an on/off state of the light source.

In one or more additional aspects, in a method according to either of the two preceding paragraphs, light from the light source may irradiate the surface in the oral cavity to promote wound healing or to control cell rhythm.

In one or more additional aspects, a method according to the preceding paragraph may further include irradiating the surface in the oral cavity with light having a wavelength of from about 370 nm to about 500 nm.

In one or more additional aspects, a method according to any of the three preceding paragraphs may further include providing an active substance in the oral cavity, and irradiating the active substance.

In one or more additional aspects, in a method according to the preceding paragraph, the active substance may include a bleaching agent, a photosensitizer, or a light-activated intercalator.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

This disclosure relates generally to oral care implements, and more particularly to oral care implements embodied as strips or patches capable of being completely retained within the oral cavity to provide a benefit to the oral cavity. Although certain embodiments and benefits will be described, other implementations, modifications, and/or benefits will be appreciated those having ordinary skill in the art, with the benefit if this disclosure.

Figure 1:
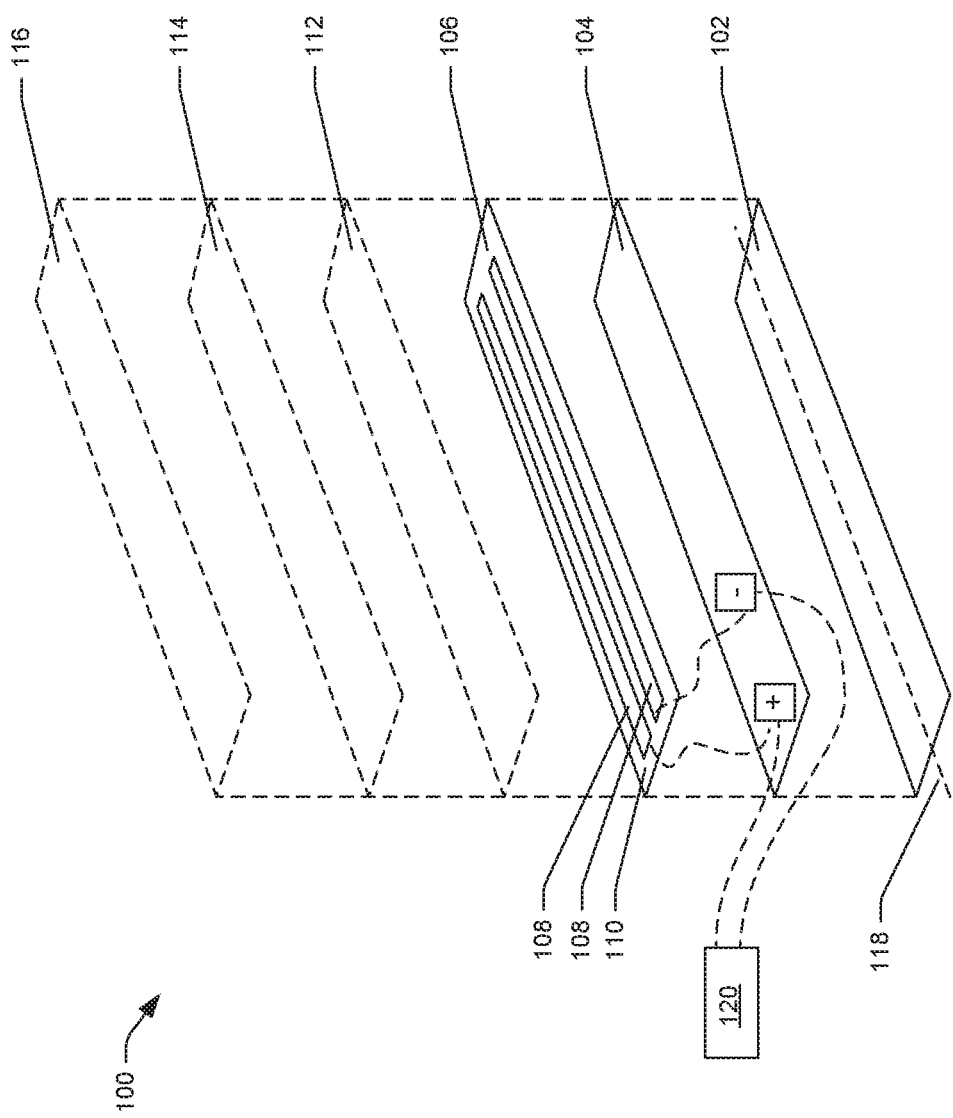
FIG. 1 is an exploded perspective view of an oral care device according to an example implementation of this disclosure.

FIG. 1 illustrates an oral care device 100 according to implementations of this disclosure. More specifically, FIG. 1. is a schematic illustration of a plurality of layers or substrates that are stacked or otherwise disposed together to form the complete device 100. In embodiments of this disclosure, the device 100 is embodied as a strip or patch sized for placement in the oral cavity. The device 100 is illustrated in FIG. 1 as having a generally rectangular shape, but this disclosure is not limited to rectangular forms. For example, the size and/or shape of the footprint of the device 100 may be varied depending upon such factors as the application, desired aesthetics, or manufacturability concerns. The strip is preferably between about 1 mm and about 5 mm thick, and more preferably about 1.5 mm to about 3 mm thick. The reduced thickness may result in more comfort for a user of the device, and may promote flexure or bending of the device, e.g., to better conform to the contours of the oral cavity.

As illustrated, the oral care device 100 includes a base layer 102, a power source 104, and an electrode layer 106. An active layer 112, an adhesive layer 114 and a release layer 116 also are illustrated in phantom lines in FIG. 1. One or more of these layers may be included in various embodiments of this disclosure.

The base layer 102 is preferably a thin, flexible substrate. As used herein, the term flexible means capable of being bent, without breaking, by manual manipulation to conform to various features of a user's oral cavity. The substrate may be made from any number of orally acceptable materials, including but not limited to, textiles, cloth, wood composite, resin, elastomer, paper, insoluble or less soluble cellulose derivatives such as ethyl cellulose and cellulose acetate, polyvinyl chloride, wax, Parafilms™, polyethylene, polyvinyl alcohol, Teflon™, polyvinyl chloride, polyvinyl acetate and their derivatives. In some instances, the flexible substrate may also or alternatively include a water-soluble polymer to promote adhesion of the device 100 to the teeth or gums. For example, the base layer 102 may include hydrophilic cellulose ethers (e.g. carboxymethyl cellulose, hydroxypropyl cellulose, hydroxypropyl methylcellulose), polyvinyl acetates, carbomers (e.g., Carbopol 97 IP), polysaccharide gums (e.g. xanthan gum), modified food starches, gelatin (e.g. animal or fish-based gelatin), cross-linked carboxyvinyl copolymers, cross-linked polyvinylpyrrolidones, polyethylene oxide (e.g., Polyox), polyacrylic acids and polyacrylates, polyvinyl alcohols, alginate, casein, pullulan, and combinations thereof.

The power source 104 is disposed on the base substrate 102, and may be a battery. The power source may be single use or rechargeable. Although several types of batteries, including button and coin batteries, may be used in accordance with principles of this disclosure, in some preferred embodiments the power source 104 comprises a flexible power source, such as a polymer battery. Polymer batteries may be preferred for their thin profile and/or their flexibility. For instance, polymer batteries may be as thick as 750 microns, or thinner. The power source 104 may be a printed battery such as a battery commercially available from Imprint Energy, Inc. of Alameda, Calif. The printed battery may include zinc screen-printed on a flexible substrate, for example.

In some embodiments, the power source 104 may be adhered to the base substrate using any known adhesive, epoxy, or the like. Alternatively, the power source 104 may include the base substrate 102. For example, some commercially available polymer batteries generally include components printed on a substrate. When such a commercially available battery is used in embodiments of this disclosure, the substrate of the battery may also act as the base substrate 102.

The electrode layer 106 generally includes a pair of electrodes 108 disposed on an electrode substrate 110. As illustrated, the electrodes 108 may include two spaced-apart conductive strips functioning as an anode and a cathode with applied current. The electrodes 108 are substantially parallel and extend generally longitudinally, i.e., parallel to a longitudinal axis 118 of the device 100. The electrodes are sufficiently thin that they can bend with, e.g., without delaminating from, the base layer 102 and the electrode substrate. The electrodes 108 may be printed or otherwise formed on the electrode substrate 110 and may comprise any number of materials including, but not limited to, tin, silver, copper, platinum, and the like. The materials comprising the electrodes preferably are chosen for their flexibility, as well as for their compatibility with the environs of the oral cavity. In some embodiments, at least one of the electrodes may be formed from a sacrificial material, such as a sacrificial metal. For example, an electrode made of zinc will oxidize upon application of current, thereby releasing $Zn^{2+}$. These zinc ions are recognized as effective anti-bacterial agents.

The electrodes 108 are attached to terminals of the power source 104. In some embodiments, the electrode 108 may be connected to the power source 104 using leads or similar conductors. In still other embodiments, the electrode layer 106 may be affixed on the power source 104 in such a manner as to create an electrical communication between the electrode 108 and the power source 104. In still other embodiments, the power source 104 and the electrodes 108 may be disposed on a common substrate, such as the base substrate 102 or the electrode substrate 110.

Although two electrodes 108 are illustrated in FIG. 1, additional electrodes 108 may also be provided. For example, the electrodes may be positioned and numbered generally to correspond with a location and number of a user's teeth.

The device 100 comprising the base substrate 102, the power source 104, and the electrode layer 106 may form a complete oral care device 100. In operation, the oral care device 100 may be placed in a user's oral cavity and current is passed through the electrodes 108 to provide an electrochemical benefit in the oral cavity. As discussed above, the benefit may constitute release of a substance upon degradation of the electrode 108. In other implementations, however, the benefit comes from a reaction with an active agent or active substance also provided in the oral cavity. In one example, the electrode may be used to activate an orally acceptable sulfate to form persulfate. The active substance or active agent may comprise a gel or paste containing a soluble and orally acceptable sulfate in a buffered, electrically conductive medium to the teeth or otherwise in the oral cavity, and the device 100 activates the sulfate in the gel or paste to form persulfate. For example, in some embodiments, an effective amount of an oral care composition comprising an orally acceptable sulfate and/or bisulfate, e.g., potassium bisulfate ($KHSO_4$), in a buffered, electrically conductive medium may be applied to the teeth, and (just before or during application) the composition is exposed to an electric potential so as to facilitate in situ production of persulfate ($S_2O_8^{2-}$), e.g., potassium persulfate ($K_2S_2O_8$).

As used herein, the term "sulfate" refers to a salt or mixture of salts formed or capable of being formed by reaction of sulfuric acid with a base. The term therefore includes bisulfate salts. The term also includes monoperoxysulfate. In aqueous solutions, there may be an equilibrium between the fully deprotonated ion (sulfate or $SO_4^{2-}$) and the partially deprotonated ion (bisulfate or $HSO_4$), and both of these ions are capable of forming persulfate when exposed to an electrical potential in an aqueous medium. "Orally acceptable sulfate" refers to sulfates (including bisulfates) which are not toxic or harmful when administered as a component of an oral care product, at relevant concentrations, e.g., 10% or less. "Soluble sulfate" refers to sulfate salts (including bisulfates) which are soluble in aqueous solution at room temperature, e.g., having a solubility of at least 10 g per 100 mL water at 25° C. The term "soluble and orally acceptable sulfate" thus encompasses, for example, compounds such as $NaHSO_4$, $KHSO_4$, $(NH_4)HSO_4$, $Mg(HSO_4)_2$, $Na_2SO_4$, $K_2SO_4$, $(NH_4)_2SO_4$, and $MgSO_4$.

Sulfates are one type of inert salts that can be activated by the electrical field in embodiments of this disclosure, e.g., to provide a whitening, anti-bacterial, or other benefit. Other types of inert salts may include chlorides, for example, which may be activated to form hyper chlorites, phosphates, which may be activated to form peroxydisphophates, peroxomonophosphates or peroxomonphosphoric acid, or carbonates, which may be activated to form peroxydicarbonate. Moreover, salts of peroxymonosulfuric acid, such as potassium peroxymonosulfate, may be oxidizing agents that can be activated by an electrical field to form powerful whitening agents.

While the device 100 may be complete with the base substrate 102, the power source 104 and the electrode layer 106, as illustrated in FIG. 1, one or more optional components may also be included. For example, the device 100 may further include the active layer 112. The active layer may include the gel or paste containing the active agent, just described. Thus, while the user can apply the active agent separately, the active layer may incorporate the active agent into the device 100. The active agent may be applied to the electrode layer 106 directly, such as by deposition, printing, painting or other known techniques. Alternatively, the active layer 112 may further include an active layer substrate that carries the active agent. In some examples, the active layer substrate may be a water-soluble polymer, which carries the active agent and may promote adhesion of the active agent to other layers of the device.

The device 100 may also or additionally include an adhesive layer 114, to promote retention of the device 100 in a desired position in the oral cavity. The adhesive layer may include any conventional orally-compatible, releasable adhesive. For example, water-soluble polymers, noted above as an example of an active layer substrate, may also be used as an adhesive in the present disclosure. As illustrated in FIG. 1, the adhesive layer 114 may have the same general footprint as the other components making up the strip. As a result, the entire strip may include adhesive. In other embodiments, less adhesive may be included. For example, only portions of the footprint of the strip may be adhesive. For instance, adhesive may be provided only at longitudinal ends of the strip, with the strip being applied much like other commercially available bandages. In other implementations, adhesive may be applied about the periphery of the strip and in still other embodiments, the adhesive layer may include a plurality of adhesion points or regions.

The oral care device 100 may also include a release layer 116. The release layer 116 may be a removable member disposed over components of the device 100, for example to prevent contamination of the oral care device 100 prior to insertion into the mouth. The release layer 116 illustrated in FIG. 1 comprises a thin sheet of flexible material, e.g., a polymeric material, that a user peels off to reveal the electrode layer, active layer, and/or adhesive layer, depending upon the construction of the device 100. When the adhesive layer 114 is present, for example, the release layer will ensure that the adhesive remains tacky until the device 100 is to be used. Although the release layer 116 is shown as a single layer, in other embodiments the release layer may instead take the form of an envelope or complete package, e.g., for completely retaining the oral care device 100 therein.

In some embodiments, the release layer 116 may also control activation of the device 100. For example, the release layer may include a physical obstruction that prevents electrical communication between the power source 104 and the electrode 108. Removing the release layer will also remove this obstruction, thereby allowing current to flow from the power source to the electrode 108. In other implementations, removal of the release layer 116 may be detected, e.g., using a presence/absence sensor, and the output from that sensor may trigger powering-up of the device.

The device 100 may also include control circuitry 120 or similar features to control the electrical circuit created by the power source 104 and the electrode 108. For example, the control circuitry 120 may alternate the polarity of the electrodes during use. Alternating the polarity may prevent accumulation of charged particles or ions on the electrodes. The control circuitry 120 may also be programmed to control an amount of current supplied to the electrode 108. The control circuitry 120 may also include a power-up function, or the like, to activate the power source 104 when the device 100 is ready for use. The control circuitry 120 may include a manual switch as part of the power-up function, such as a toggle or push button switch. Moreover, as discussed above, the release layer 116 could also be integrated into the power-up function, e.g., such that removal of the release layer 116 powers up the device 100. In other embodiments, the control circuitry 120 may include sensor outputs. For example, a conventional presence/absence sensor could be disposed to be covered by the release layer 116, and detect removal of the release layer 116. This detection could then be used to turn on the device 100. In another embodiment, a water- or liquid moisture-detecting sensor may be provided. When the sensor comes in contact with saliva, i.e., upon being inserted into the mouth, the power source 104 is turned on. The control circuitry 120 could be provided on a separate layer, or could be integrated into another layer. For example, it may be desirable to incorporate the control circuitry 120 into the electrode layer 106, the base layer 102, and/or the power source layer.

As will be appreciated, the oral care device 100 is generally a thin, flexible device capable of simple insertion into the oral cavity. Depending upon the benefit to be achieved from the device, the device may be placed over one or more teeth, on the gums, on the inside of the cheek, and/or on or under the tongue. When the device is used to treat teeth, e.g., in the sulfate/persulfate example noted above, it may be desirable to situate the electrodes as close to the teeth as possible. Because the device is flexible, in some examples the device can be folded, for example, proximate the longitudinal axis 118, such that device can be placed around one or more teeth with one of the electrodes 108 in front of the tooth/teeth and the other of the electrodes 108 disposed behind the tooth/teeth. In this manner, the electrical field generated at the electrodes 108 would pass through the tooth/teeth disposed between the spaced electrodes 108. This arrangement disposes the electrodes in intimate contact with the teeth. Such an arrangement may also be beneficial to drive ions, such as $Fl^-$ or $Ca^{2+}$ ions, into the tooth enamel.

Thus, in some embodiments, this disclosure provides a complete, electrode-based oral care device capable of providing benefit to the oral cavity without the need for external (to the oral cavity) components. The overall thickness of the device 100 is preferably less than about 2 mm.

Figure 2:
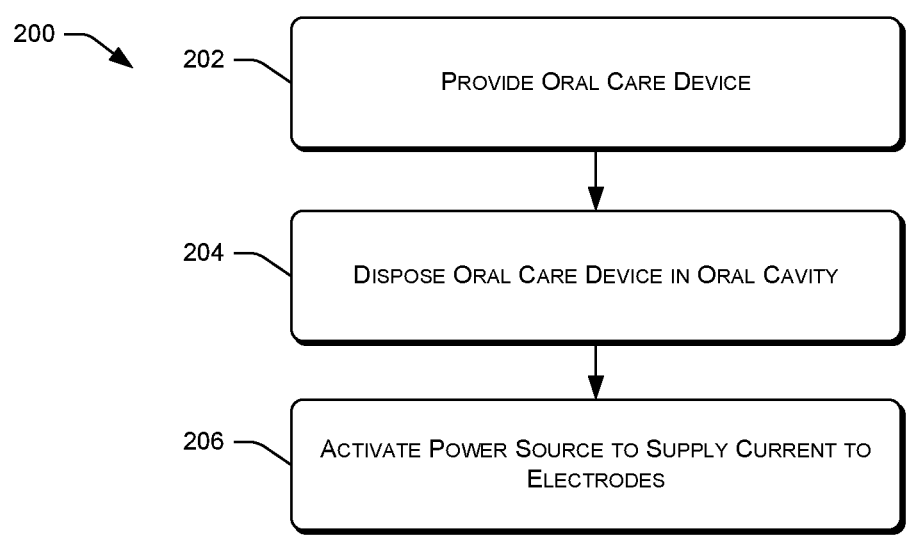
FIG. 2 is a schematic illustration of an example method of using an oral care device such as the device illustrated in FIG. 1.

FIG. 2 is a flow chart depicting an example process 200 for using the device 100 just described.

In the process 200, at 202, an oral care device such as the oral care device 100 is provided. At 204, the oral care device is placed in the oral cavity, proximate a portion of the oral cavity to be treated. When tooth whitening or enamel strengthening is the desired objective, the device 100 is preferably placed in intimate contact with the tooth or teeth to be treated. 204 may include bending or folding the oral care device to promote this intimate contact, e.g., in the manner described above. The adhesive layer 114 described above, may be provided to promote placement and retention of the device 100 at the desired location in the oral cavity. At 206, the oral care device is activated, to allow current to flow through the electrodes and obtain the desired electrochemical benefit.

The process 200 may include additional steps, such as introducing an active substance into the oral cavity. The active substance may be provided as part of the device, or may be applied separately, as described in more detail, above.

Figure 3:
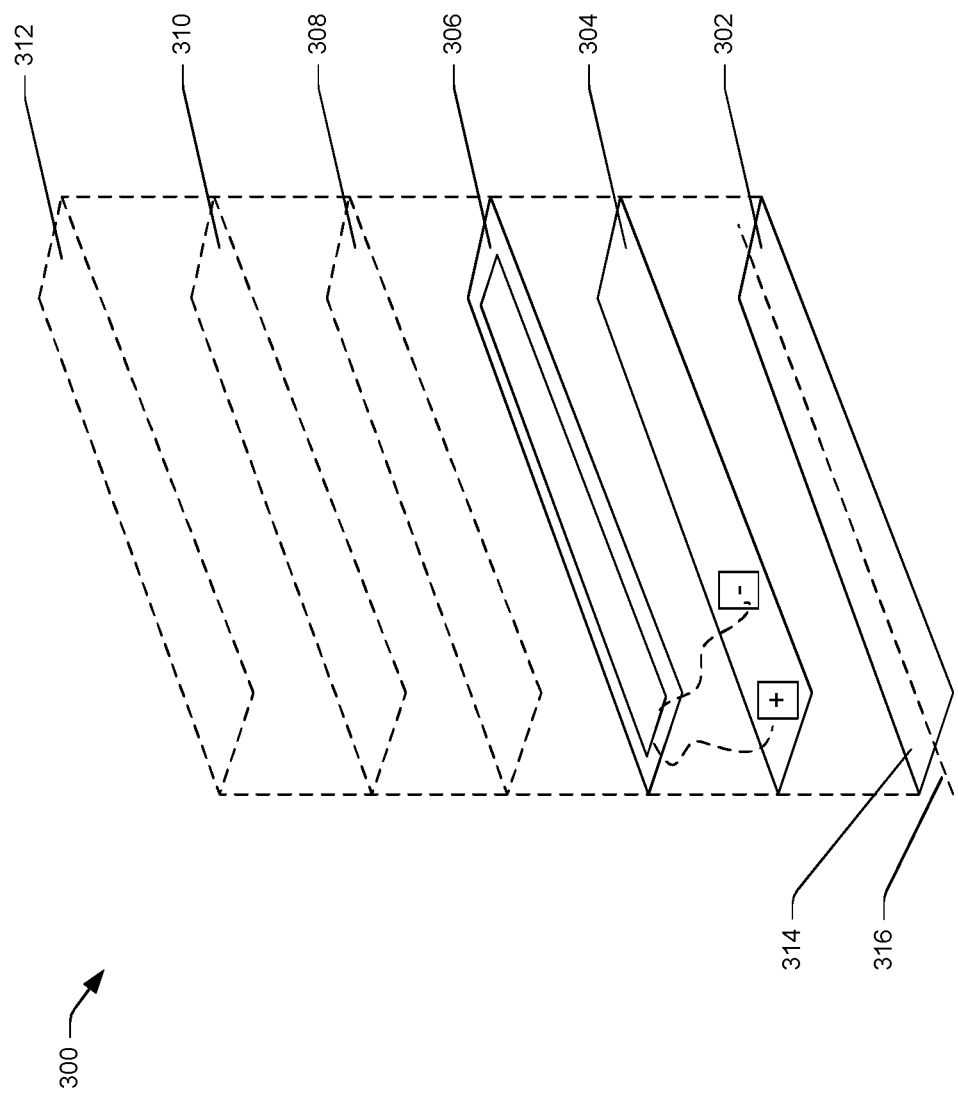
FIG. 3 is an exploded perspective view of another oral care device according to another example implementation of this disclosure.

FIG. 3 illustrates another thin, flexible, layered oral care device 300. The oral care device 300 is similar to the oral care device 100 in that it includes a base substrate 302 and a power source 304 disposed on the base substrate 302. Unlike the oral care device 100, however, the oral care device 300 includes a flexible light source 306. As also illustrated in FIG. 3, the device 300 may optionally include one or more of an active substrate 308, an adhesive layer 310, and a release layer 312.

The base substrate 302 may be similar to the base substrate 102 described above. The base substrate may be chosen to provide a platform upon which other components may be disposed, and is preferably thin, e.g., less than about 500 microns and flexible. The base substrate may be a thin flexible polymer, for example. The base substrate 302 may also include a reflective surface 314, the function of which will be described in more detail, below. The reflective surface 314 may be a film or other coating disposed on the base substrate 302, or the material of the base substrate may be chosen for its reflectivity.

The power source 304 may be any number of power sources, including those described above with respect to the oral care device 100. In preferred embodiments, the power source may be one or more polymer batteries, which may be chosen for their thin profile and flexibility. As with the examples discussed above, a substrate of the power source 304 may also act as the base substrate 302 in some embodiments.

As illustrated in FIG. 3, the light source is represented as a thin layer. In preferred embodiments, the light source 306 includes one or more polymer light emitting diodes (PLEDs) and/or flexible organic LEDs (FOLEDs) and/or printed LEDs. These lighting technologies may be preferred for their thin, flexible forms. The light source is powered by the power source 302 through one or more electrical connections. Such connections may be leads, soldering, or the like. Power to the light source 306 allows for emission of light, and the reflective surface 314 preferably is disposed to direct substantially all light away from the base substrate 302.

The oral care device 300 made up of only the base substrate 302, the power source 304, and the light source 306 may serve as a beneficial oral care tool. For example, the inventors have discovered that the radiation of active whitening agents at a wavelength range of 370 to 500 nm enhances whitening of stained tooth enamel. PLEDs and FOLEDs can emit light in that wavelength range. Because of its flexible nature, the device 300 may be wrapped around a user's teeth, such as by folding the device 300 along a longitudinal axis 316, much like in the manner described above with respect to the device 100, to achieve irradiation of substantially all of the tooth.

Light therapy may also be beneficial for wound healing purposes. Accordingly, a user may apply the device 300 over a wounded portion of the oral cavity and the device 300 will irradiate the wound with light of a selected wavelength. Various studies have shown that such radiation therapy can enhance blood flow, thereby leading to greater healing benefit. In other embodiments, the device 300 may be used in the oral cavity to alleviate dry mouth and/or bad breath. For example, by pulsing the light emitted by the light source 306, it may be possible to activate cells in the oral cavity, such as while a user sleeps at night. Such a practice may promote more beneficial cell behavior.

Although not illustrated, the device 300 may also include control circuitry to control the light emitted from the light source. For example, control circuitry may execute a timing pattern useful for varying one or more of the wavelength of emitted light, intensity of emitted light, an on/off state of the light source, and/or the like. The control circuitry may be provided on a separate substrate, on the base substrate 302, integrated into either or both of the power source 304 and/or the light source layer 306, or some combination thereof.

The device 300 may also include additional layers or components. For example, a noted use above is to irradiate stained enamel in the presence of active whitening agents. These agents may include hydrogen peroxide or other bleaching agents, such as peroxydisulfate, peroxydiphosphate, percarbonate, and others. In some implementation the user may be required to apply or otherwise introduce the agents into the oral cavity. Or, the active whitening agents may be provided as a part of the device 300, e.g., in the form of the active substrate 308. A slurry, gel, or paste containing a to-be-irradiated active ingredient may be directly deposited on the light source 306, or may be provided as part of a substrate that is adhered or otherwise attached to the light source 306. For example, the active substrate may include a polymer-based layer upon which the active ingredient is carried. The polymer base layer may then be adhered or otherwise secured to or proximate the light source 306. As will be appreciated, the carrier for the active ingredient may be substantially transparent, so as not to interfere with the radiating light emitted from the light source 304. In some examples, the polymer substrate may include a water-soluble polymer, which may promote adhesion of the active substrate to the light source and/or to the teeth or other surface in the oral cavity.

Active agents, other than bleaching agents, may alternatively be provided in the active substrate 308. For example, the active substrate may include a DNA or RNA light activated intercalator. By irradiating the intercalator with the light source, specific sequences can be destroyed, thereby potentially suppressing specific bacteria and/or protein expressions. In other embodiments, the active substrate may include a photosensitizer, and the device may then directly deliver the photosensitizer to one or more specific sites in the oral cavity. The combination of light and photosensitizer gives rise to reactive oxygen species that have been shown to treat periodontal and peri-implant diseases.

In some embodiments, the device 300 may also include the adhesive layer 310 and/or the release layer 312. The adhesive layer 310 the release layer 312 may be similar to the adhesive layer 114 and the release layer 116 described above, and will not be described again in detail herein.

Other modifications to the device 300 also are contemplated. For example, although the reflective surface 314 is illustrated as being on a surface of the base substrate, the positioning of the reflective surface 314 may vary. For example, it may be beneficial to dispose the reflective surface between the light source and the power source. Preferably, the reflective surface 314 is disposed to maximize the use of the irradiating light on the location to be irradiated.

Figure 4:
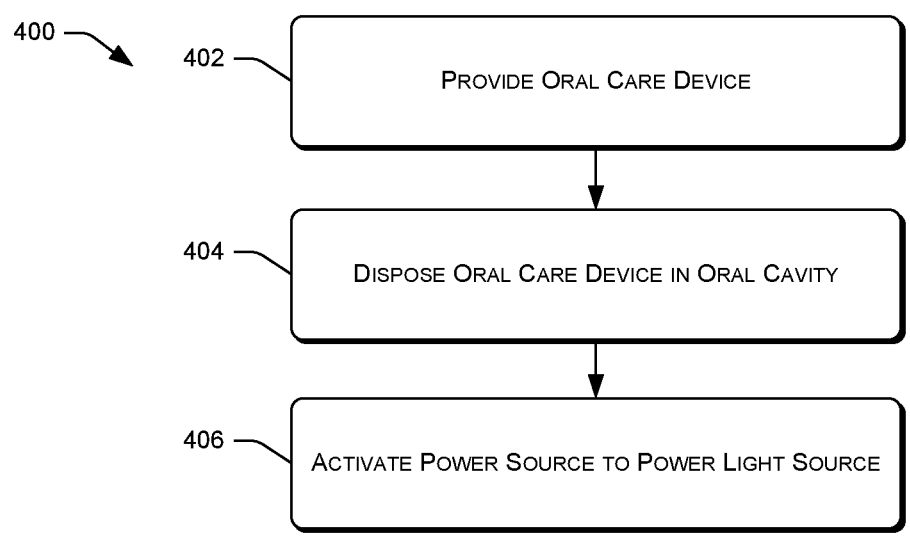
FIG. 4 is a schematic illustration of an example method of using an oral care device such as the device illustrated in FIG. 3.

FIG. 4 is a flow chart depicting an example process 400 for using the device 300 just described.

In the process 400, at 402, an oral care device such as the oral care device 300 is provided. At 404, the oral care device is placed in the oral cavity, proximate a surface of the oral cavity to be irradiated by the light source. As will be appreciated, the device 300 is generally placed with the light source closer to the surface to be irradiated, e.g., between the surface to be irradiated and the base layer 302. When tooth whitening is the desired objective, the device 300 is preferably placed in intimate contact with the tooth or teeth to be treated. 404 may include bending or folding the oral care device to promote this intimate contact, e.g., in the manner described above. The adhesive layer 310 described above, may be provided to promote placement and retention of the device 300 at the desired location in the oral cavity. At 406, the oral care device is activated, to power the light source and irradiate a surface in the oral cavity.

The process 400 may include additional steps, such as introducing an active substance into the oral cavity. The active substance may be provided as part of the device, or may be applied separately, as described in more detail, above. The process 400 may also include controlling the irradiating light, e.g., controlling a wavelength, an irradiation time period, or the like.

The present disclosure describes compact oral care devices that are effective and relatively simple to use. The devices described herein provide powered strips that allow a user to perform oral care procedures that previously required external light and/or power sources. Other modifications, combinations, enhancements and benefits will be appreciated by those having ordinary skill in the art, with the benefit of this disclosure. For example, although the device 100 includes electrodes 108 in electrical communication with a power source and the device 300 includes a light source 306 in electrical communication with a power source, a hybrid device also is contemplated. For example, another embodiment may include both one or more electrodes and a light source. In this way, benefits from both electrochemistry and from irradiation may be realized in a single device. In such a multi-functional device, it may be desirable to place the electrodes between the light source and the base substrate, e.g., to reduce interference with the irradiating light. To this end, the reflective surface may be arranged to cover the electrodes.

Moreover, the flexible devices described herein may be used in connection with additional structure. For example, the devices may be placed in a more rigid form, such as a tray or mouth guard. In this manner, the device may be kept in close proximity to the teeth, for example. The use of a tray or mouth guard may obviate the need for an adhesive in some instances.

The term "sulfate" as used herein, means a salt or mixture of salts formed or capable of being formed by reaction of sulfuric acid with a base. The term therefore includes bisulfate salts. In aqueous solutions, there may be an equilibrium between the fully deprotonated ion (sulfate or $SO_4^{2-}$) and the partially deprotonated ion (bisulfate or $HSO_4$), and both of these ions are capable of forming persulfate when exposed to an electrical potential in an aqueous medium. "Orally acceptable sulfate" refers to sulfates (including bisulfates) which are not toxic or harmful when administered as a component of an oral care product, at relevant concentrations, e.g., 10% or less. "Soluble sulfate" refers to sulfate salts (including bisulfates) which are soluble in aqueous solution at room temperature, e.g., having a solubility of at least 10 g per 100 mL water at 25° C. The term "soluble and orally acceptable sulfate" thus encompasses, for example, compounds such as $NaHSO_4$, $KHSO_4$, $(NH_4)HSO_4$, $Mg(HSO_4)_2$, $Na_2SO_4$, $K_2SO_4$, $(NH_4)_2SO_4$, and $MgSO_4$.

As used herein, "in situ" means that the persulfate is generated in the oral care product just before or during use and is not added as a separate ingredient.

As used herein, "effective amount" means an amount or concentration effective to perform the desired function when the product is used. Thus an effective amount of sulfate refers to an amount of a sulfate salt (e.g., selected from sodium bisulfate, potassium bisulfate, ammonium bisulfate, magnesium bisulfate, sodium sulfate, potassium sulfate, ammonium sulfate, magnesium sulfate, and mixtures thereof) which, when activated by an electrical current to form persulfate, provides persulfate in an amount or concentration effective to whiten the teeth.

Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:

1. An oral care device configured for placement in an oral cavity comprising:
    a flexible base substrate;
    a flexible power source disposed on a surface of the base substrate; and
    an electrode layer disposed on the surface of the flexible base substrate or the flexible power source, the electrode layer comprising an electrode substrate, a first electrode comprising a first flexible metallic strip electrically connected to the flexible power source, and a second electrode comprising a second flexible metallic strip electrically connected to the flexible power source, wherein the first and second electrodes are located on a first side of the electrode substrate and the flexible power source is located on an opposite second side of the electrode substrate;
    wherein the first and second electrodes have a polarity which is alternated during use.

2. The oral care device of claim 1, wherein at least one of the first electrode and the second electrode comprises a sacrificial metal that degrades upon application of current to the first electrode and the second electrode to release ions to the oral cavity.

3. The oral care device of claim 2, wherein the sacrificial metal comprises zinc, and the zinc oxidizes upon application of current to the first electrode and the second electrode to release zinc ions.

4. The oral care device of claim 1, further comprising an active substance.

5. The oral care device of claim 4, wherein the active substance comprises at least one of a tooth whitener or an anti-bacterial.

6. The oral care device of claim 5, wherein the active substance comprises a persulfate, a monoperoxy sulfate, a chloride, a phosphate, or a carbonate.

7. The oral care device of claim 4, wherein the active substance is formed as a paste or gel and disposed on a side of the first electrode and the second electrode opposite the flexible base substrate.

8. The oral care device of claim 4, wherein the active substance is disposed on an active layer substrate, and the active layer substrate is disposed on a side of the first electrode and the second electrode opposite the flexible base substrate.

9. The oral care device of claim 1, further comprising an adhesive layer disposed to retain the oral care device in a position in the oral cavity.

10. The oral care device of claim 1, further comprising a removable release layer.

11. The oral care device of claim 10, wherein the release layer is disposed over an adhesive, and removal of the release layer exposes the adhesive.

12. The oral care device of claim 1, wherein the flexible power source is a polymer battery.

13. The oral care device of claim 1, further comprising control circuitry in electrical communication with the power source to control current between the flexible power source and the first and second electrodes.

14. The oral care device of claim 13, wherein the control circuitry controls an amount of current supplied to the first and second electrodes.

15. An oral care device configured for placement in an oral cavity comprising:
    a flexible base substrate;
    a flexible power source disposed on a surface of the base substrate;
    an electrode layer disposed on the surface of the flexible base substrate or the flexible power source, the electrode layer comprising an electrode substrate, a first electrode comprising a first flexible metallic strip electrically connected to the flexible power source, and a second electrode comprising a second flexible metallic strip electrically connected to the flexible power source, wherein the first and second electrodes are located on a first side of the electrode substrate and the flexible power source is located on an opposite second side of the electrode substrate; and
    a removable release layer;
    wherein the release layer is disposed such that removal of the release layer automatically activates the flexible power source or closes a circuit between the flexible power source, the first electrode and the second electrode.

16. The oral care device of claim 15, wherein removal of the release layer triggers an output from a sensor that powers up the device.

17. The oral care device of claim 15, wherein removal of the release layer removes a physical obstruction that prevents electrical communication between the power source and one of the first and second electrodes.

18. A method of treating a condition in an oral cavity comprising:
providing a flexible oral care device comprising a flexible base substrate, a flexible power source disposed on a side of the base substrate, an electrode substrate, a first electrode comprising a first flexible metallic strip electrically connected to the power source, and a second electrode comprising a second flexible metallic strip electrically connected to the power source, the second electrode parallel to the first metallic strip, the first and second electrodes being located on a first side of the electrode substrate and the flexible power source located on an opposite second side of the electrode substrate;
retaining the flexible oral care device on a surface in the oral cavity; and
powering on the flexible power source to generate an electrical field between the first electrode and the second electrode.

19. The method of claim 18, further comprising providing an active substance in the oral cavity, proximate to at least one of the first electrode and the second electrode.

20. The method of claim 19, wherein the active substance comprises an active layer disposed on the flexible oral care device.

21. The method of claim 19, wherein the active agent comprises an inert salt that generates a whitening agent in the electrical field.

22. The method of claim 21, wherein the inert salt comprises a sulfate that generates persulfate in the electrical field.

23. The method of claim 18, further comprising folding the flexible oral care device along a longitudinal axis between a first longitudinal side of the flexible oral care device and a second longitudinal side of the flexible oral care device, and
wherein the retaining the flexible oral care device on the surface of the oral cavity comprises retaining a portion of the first longitudinal side of the flexible oral care device on a first side of at least one tooth in the oral cavity and retaining a portion of the second longitudinal side of the flexible oral care device on a second side the at least one tooth.

24. The method of claim 18, wherein the flexible oral care device further comprises a release layer and powering on the flexible power source comprises removing the release layer.

25. The method of claim 18, wherein one of the first electrode and the second electrode comprises zinc.

26. An oral care device configured for placement in an oral cavity comprising:
a flexible base substrate;
a flexible power source disposed on a surface of the base substrate; and
an electrode layer disposed on the flexible power source, the electrode layer comprising an electrode substrate overlying the flexible power source, a first electrode disposed on the electrode substrate and comprising a first flexible metallic strip electrically connected to the flexible power source, and a second electrode disposed on the electrode substrate and comprising a second flexible metallic strip electrically connected to the flexible power source;
wherein the first and second electrodes are located on a first side of the electrode substrate and the flexible power source is located on an opposite second side of the electrode substrate.

27. The oral care device of claim 26, wherein the first and second electrodes have a polarity which is alternated during use.

28. The oral care device of claim 26, wherein the flexible power source overlies the base substrate, the electrode substrate of the electrode layer overlies the flexible power source, and the first and second electrodes of the electrode overlie the electrode substrate.

29. The oral care device of claim 26, wherein the flexible power source is in surface contact with the base substrate and the electrode substrate of the electrode layer.

* * * * *